United States Patent
Shahriari

(10) Patent No.: US 7,740,904 B2
(45) Date of Patent: Jun. 22, 2010

(54) HIGH PERFORMANCE MATERIALS FOR OPTICAL SENSORS FOR HYDROCARBONS ENVIRONMENT

(75) Inventor: Mahmoud R. Shahriari, Palm Harbor, FL (US)

(73) Assignee: Ocean Optics, Inc., Dunedin, FL (US)

( * ) Notice: Subject to any disclaimer, the term of this patent is extended or adjusted under 35 U.S.C. 154(b) by 999 days.

(21) Appl. No.: 11/483,573

(22) Filed: Jul. 10, 2006

(65) Prior Publication Data

US 2007/0122311 A1    May 31, 2007

Related U.S. Application Data

(60) Provisional application No. 60/698,152, filed on Jul. 11, 2005.

(51) Int. Cl.
*G01N 21/64* (2006.01)
(52) U.S. Cl. .................. 427/157; 427/8; 427/372.2
(58) Field of Classification Search .............. 427/8, 427/157, 372.2
See application file for complete search history.

(56) References Cited

U.S. PATENT DOCUMENTS 5,047,350 A * 9/1991 Switalski et al. ............ 436/136

2001/0039766 A1 * 11/2001 Hattori et al. ................. 51/308

OTHER PUBLICATIONS

McDonagh, C. et al., "Tailoring of Sol-Gel Films for Optical Sensing of Oxygen in Gas and Aqueous Phase", Analytical Chemistry, 70, 45-50, 1998.*

* cited by examiner

*Primary Examiner*—Timothy H Meeks
*Assistant Examiner*—James Lin
(74) *Attorney, Agent, or Firm*—Dennis L. Cook, Esq.

(57) ABSTRACT

This invention belongs to the field of optical chemical sensors. Specifically, it relates to sensors based on the absorbance and emission of light by an indicator molecule where the optical properties of the indicator molecule change in response to a particular analyte. These indicator molecules are immobilized in a transparent substance that is exposed to light, where the substance is typically a solid such as a sol-gel or a polymer. More specifically, it is a new process for manufacturing a material (a medium or matrix) to hold or encapsulate sensing molecules. This new material has an improved resistance to exposure to hydrocarbons. These materials are used to immobilize colorimetric and/or fluorescence indicators in a matrix that repels hydrocarbons in general and non-polar hydrocarbons (i.e. aromatics hydrocarbons) in particular.

6 Claims, 2 Drawing Sheets

Figure 1

| Sample | % intensity decay in 20 hours | % τ (fluorescence lifetime) change in jet fuel in 24 hours |
|---|---|---|
| Standard formulation | 20 % | 4.5% |
| Modified sol-gel doping | 4 % | <1% |

Table on Effect of sol-gel modification on the intensity decay in 20 hours in jet fuel vapor (Air saturated with jet fuel)

HIGH PERFORMANCE MATERIALS FOR OPTICAL SENSORS FOR HYDROCARBONS ENVIRONMENT

CROSS-REFERENCE TO RELATED APPLICATION

The present application claims the benefit of previously filed Provisional Patent Application, Ser. No. 60/698,152 filed on Jul. 11, 2005.

FIELD OF THE INVENTION

This invention belongs to the field of optical chemical sensors. Specifically, it relates to sensors based on the absorbance and emission of light by an indicator molecule where the optical properties of the indicator molecule change in response to a particular analyte. These indicator molecules are immobilized in a transparent substance that is exposed to light, where the substance is typically a solid such as a sol-gel or a polymer. More specifically, it is a new process for manufacturing a material (a medium or matrix) to hold or encapsulate sensing molecules. This new material has an improved resistance to exposure to hydrocarbons. These materials are used to immobilize colorimetric and/or fluorescence indicators in a matrix that repels hydrocarbons in general and non-polar hydrocarbons (i.e. aromatics hydrocarbons and aliphatic hydrocarbons) in particular. An example is the immobilization of a ruthenium organic compound, which is used to sense molecular oxygen. The new material or matrix is resistant, or impermeable to the hydrocarbons in fuels such as jet fuel, gasoline or any hydrocarbon used in a combustion process. The new material, while resistant to hydrocarbons, is none-the-less still permeable to oxygen. The fluorescence material is mixed with the sol-gel monomers and then coated on the tip of an optical fiber. The sol-gel polymerizes, trapping the ruthenium compound in an oxygen permeable, hydrocarbon impermeable glass like solid. The high resistance of the sol-gel matrix toward fuel and high permeability toward oxygen make it an ideal sensor material for monitoring the oxygen dissolved in liquid hydrocarbon fuels as well as in the oxygen in the fuel headspace inside of fuel tanks.

More specifically, the sol-gel support medium resulting from this invention can be used as a platform for making a number of sensors for monitoring gases, and dissolved gases in a wide range of hydrocarbon liquids and vapors. There is a lack of effective optical sensors available for monitoring gasses in many fuels including jet, diesel and gasoline fuels. For example a fiber optic oxygen probe resulting from this invention can be used to monitor oxygen in a military and commercial fuel tank as part of an On Board Inerting Gas System (OBIGS) to protect the fuel tank from explosion. Other applications include: Oxygen monitoring in organic solvents, Oxygen monitoring during polymerization process, Oxygen monitoring in hydrocarbon streams, Oxygen monitoring during wine or alcohol fermentation, automotive fuel monitoring, and Oxygen monitoring in vegetable, tallow, or other oil.

BACKGROUND OF THE INVENTION

Indicator Molecules Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," Analytical Chemistry, Vol. 56, No. 1, January 1984, each of which is incorporated by reference herein.

More generally, luminophores have been used to facilitate optical sensing. As used herein, a "luminophore" is a chemical species which reacts to the presence of a substance to produce an optical result. A fluorophore is thus one type of luminophore. Another type of luminophore changes color in accordance with changes in the amount of a substance of interest. A sensor which utilizes this principle to detect pH and $CO_2$ is disclosed in Weigl, Holobar, Trettnak, Klimant, Kraus, O'Leary, and Wolfbeis, Optical Triple Sensor for Measuring pH, Oxygen and Carbon Dioxide, 32 JOURNAL OF BIOTECHNOLOGY 127 (1994)

For oxygen sensors, a ruthenium-based compound or "ruthenium complex" has been used as the fluorophore to provide the requisite fluorescence. The use of ruthenium complexes in oxygen sensors has been described in the following publications: Hartman, Leiner and Lippitsch, Luminescence Quenching Behavior of an Oxygen Sensor Based on a Ru(II) Complex Dissolved in Polystyrene, 67 ANAL. CHEM. 88 (1995); Carraway, Demas, DeGraff, and Bacon, Photophysics and Photochemistry of Oxygen Sensors Based on Luminescent Transition-Metal Complexes, 63 ANAL. CHEM. 337 (1991); and Bacon and Demas, Determination of Oxygen Concentrations by Luminescence Quenching of a Polymer-Immobilized Transition-Metal Complex, 59 ANAL. CHEM. 2780 (1987). In addition to ruthenium complexes, other fluorophores have also been used to detect oxygen, as described in the following publications: Wolfbeis, Posch and Kroneis, Fiber Optical Fluorosensor for Determination of Halothan and/or Oxygen, 57 ANAL. CHEM. 2556 (1985); and Wolfbeis, Offenbacher, Kroneis and Marsoner, A Fast Responding Fluorescence Sensor for Oxygen, I MIKROCHIMICA ACTA EEWIEN! 153 (1984). U.S. Pat. No. 5,176,882 to Gray et al., U.S. Pat. No. 5,155,046 to Hui et al., and U.S. Pat. No. 4,861,727 to Hauenstein et al. also disclose various fluorophores which may be used to detect oxygen.

Such indicator molecules are specific in their excitation and emission wavelengths. The fluorescent emission from an indicator molecule may be attenuated or enhanced by the local presence of the molecule being analyzed. For example, a tris(4,7-diphenyl-1,10-phenanthroline)ruthenium (II) perchlorate molecule particular for oxygen sensing is excited by shining light onto the substance at 460 nm (blue). The molecule's fluorescent emission immediately occurs at 620 nm (orange-red). However, the emission is quenched by the local presence of oxygen interacting with the indicator molecule, to cause the intensity of the fluorescence to be related to the ambient oxygen concentration. Consequently, the more oxygen that is present, the lower the emission intensity and vice-versa and when zero or no oxygen is present, the maximum fluorescent intensity of emitted light is present.

The quenching of the luminescence of an emitter at the end of an optical fiber has also been used in temperature sensors. For temperature probes the emitters are generally solid phosphors rather than an aromatic molecule embedded in plastic, since access by molecules from the environment is not desirable. Various methods have been used to measure the amount of quenching: (i) Quick et al. in U.S. Pat. No. 4,223,226 ratios the intensity at one wavelength of the emission against another; (ii) Quick et al. also proposes determining the length of time it takes for the signal to fall from one level to another;

(iii) Samulski in U.S. Pat. No. 4,245,507 (reissued as U.S. Pat. No. Re. 31,832) proposes to measure quenching by determining the phase of the emitted life. In a patent for temperature sensing at the end of an optical fiber, Hirschfeld in U.S. Pat. No. 4,542,987 proposes, in addition to method (i), that (iv) emission lifetime be used to measure quenching and that (v) Raman scattered light can be used as a reference.

Compounds other than those containing ruthenium are also known. Eastwood and Gouterman (1970) noted generally with respect to Pd and Pt porphyrin complexes that their "relatively high emission yields and short triplet lifetimes . . . may make these systems useful as . . . biological probes for the presence of oxygen." More recently, Bacon and Demas in UK Patent Application No. 2,132,348A propose the use of, inter alia, porphyrin complexes of $VO_2+$, $Cu_2+$, $Pt_2+$, $Zn.sup.2+$ and $Pd_2+$ or dimeric Rh, Pt, or Ir complexes for monitoring oxygen concentration by emission quenching of intensity or lifetime. Suitable ligands would reportedly be etioporphyrin, octaethylporphin, and porphin.

The fluorescence of the indicator molecules employed in the device described in U.S. Pat. No. 5,517,313 is modulated, e.g., attenuated or enhanced, by the local presence of the analyte. For example, the orange-red fluorescence of the complex, tris(4,7-diphenyl-1,10-phenanthroline)ruthenium(II) perchlorate is quenched by the local presence of oxygen. This complex can, therefore, advantageously be used as the indicator molecule of an oxygen sensor. Similarly, other indicator molecules whose fluorescence is affected by specific analytes are known.

Optical Sensing Devices These fluorescent indicators described above have classically been used in fluorescence spectrophotometers. These instruments are designed to read fluorescence intensity and/or the decay time of fluorescence. The indicator molecules and samples are classically in a solution or liquid phase and are assayed in discrete measurements made on individual samples contained in cuvettes.

Fluorescence indicators trapped in a solid substance typically are deposited as a thin layer or a membrane onto a fiber optic waveguide, the waveguide and trapped analyte forming a fiber optic sensor. The sensor is introduced to the sample in a manner such that the indicator will interact with the analyte. This interaction results in a change in optical properties, as discussed above, where this change is probed and detected through the fiber optic waveguide by an optical detector. The optical detector can be a single photodetector with an optical filter, a spectrometer, or any optical detection system capable of measuring light intensity or the change in light intensity through time. These optical properties of chemical sensor compositions typically involve changes in colors or in color intensities, or fluorescence intensity or fluorescence lifetime. In these types of sensors, it is possible to detect changes in the analytes being monitored at the tip of the fiber sensor by a detector which is located remotely to the sample, in order to thereby provide remote monitoring capabilities. In such systems, the amount of light reaching the detector will limit the sensitivity and signal to noise of the analyte measurement.

A second area of fluorescence sensor state-of-the-art is in fiber optic devices. These sensor devices allow miniaturization and remote sensing of specific analytes. The fluorescent indicator molecule is immobilized via mechanical or chemical means to one end of an optical fiber. To the opposite end of the fiber is attached a fiber coupler (Y shaped fiber) or a beam splitter. Incident excitation light is coupled into one leg of the fiber typically via a filter and a lens. Excitation light is carried via the fiber to the distal end where the fluorescent indicator molecule is immobilized to the tip.

Upon excitation, the indicator molecule uniformly radiates the fluorescent light, some of which is recaptured by the fiber tip and propagated back through the fiber to the Y junction or "coupler". At the junction, a substantial portion (typically half) of the fluorescence is conveyed back to the emitter or point of origin thereby unavailable for signal detection. To offset the inefficiencies of the system, lasers are often used to raise the input power and highly sensitive photomultiplier tubes are used as detectors thereby raising costs by thousands of dollars. The other half travels along the other leg of the Y to the detector and is recorded.

U.S. Pat. No. 6,024,923 issued to Melendez et al. on Feb. 15, 2000 entitled Integrated Fluorescence-Based Biochemical Sensor, discloses an integrated biochemical sensor for detecting the presence of one or more specific samples having a device platform with a light absorbing upper surface and input/output pins. An encapsulating housing provides an optical transmissive enclosure which covers the platform and has a layer of fluorescence chemistry on its outer surface. The fluorophore is chosen for its molecular properties in the presence of the sample analyte. The detector and light sources are all coupled to the platform and encapsulated within the housing. A filter element is used to block out unwanted light and increase the detector's ability to resolve wanted emission light.

U.S. Pat. No. 5,910,661 issued to Colvin, Jr. on Jun. 8, 1999 entitled Fluorescence Sensing Device discloses a fluorescence sensing device for determining the presence or concentration of an analyte in a liquid or gaseous medium. The device is constructed of an optical filter, which is positioned on a photodetector and which has a thin film of analyte-permeable, fluorescent indicator molecule-containing material on its top surface. An edge-emitting, light-emitting P-N junction is positioned on the top surface of the optical filter such that the P-N junction from which light is emitted is positioned within the film. Light emitted by the fluorescent indicator molecules impacts the photodetector thereby generating an electrical signal that is related to the concentration of the analyte in the liquid or gaseous medium. Fluorescence sensing devices according to this invention are characterized by very compact sizes, fast response times and high signal-to-noise ratios.

U.S. Pat. No. 5,517,313, also issued to Colvin describes a fluorescence sensing device comprising a layered array of a fluorescent indicator molecule-containing substance, a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source.

None of these devices, however, incorporate a highly resistant medium for the encapsulation of an optical sensor material thereby enabling the use of said sensor in harsh environments containing solvent hydrocarbon compounds.

Optical Sensors for Use in Detecting Oxygen Because oxygen is a triplet molecule, it is able to quench efficiently the fluorescence and phosphorescence of certain luminophores. This effect (first described by Kautsky in 1939) is called "dynamic fluorescence quenching." Collision of an oxygen molecule with a fluorophore in its excited state leads to a non-radiative transfer of energy. The degree of quenching is related to the frequency of collisions, and therefore, to the concentration, pressure and temperature of the oxygen-containing media.

There are several issued patents that concern optical sensors designed to sense the presence of oxygen in addition to those devices described above.

An oxygen sensor based on oxygen-quenched fluorescence is described in U.S. Pat. Reissue No. 31,879 to Lubbers et al. Lubbers et al. describe an optrode consisting of a light-transmissive upper layer coupled to a light source, an oxygen-permeable lower diffusion membrane in contact with an oxygen-containing fluid, and a middle layer of an oxygen-quenchable fluorescent indicating substance, such as pyrenebutyric acid. When illuminated by a source light beam of a predetermined wavelength, the indicating substance emits a fluorescent beam of a wavelength different from the source beam and whose intensity is inversely proportional to the concentration of oxygen present. The resultant beam emanating from the optode, which includes both a portion of the source beam reflected from the optrode and the fluorescent beam emitted by the indicating substance, is discriminated by means of a filter so that only the fluorescent beam is sent to the detector. In a second embodiment, the optrode consists of a supporting foil made of a gas-diffusable material such as silicone in which the fluorescent indicating substance is randomly mixed, preferably in a polymerization type reaction, so that the indicating substance will not be washed away by the flow of blood over the optode.

U.S. Pat. No. 3,612,866 to Stevens describes a method of calibrating an oxygen-quenchable luminescent sensor. The Stevens device includes an oxygen-sensitive luminescent sensor made of pyrene and, disposed adjacent thereto, an oxygen-insensitive reference sensor also made of pyrene but which is covered with an oxygen-impermeable layer. The oxygen concentration is evaluated by comparing the outputs of the measuring and reference sensors.

Substances Indicator molecules that are incorporated at the distal end of fiber optic sensors are often configured as membranes that are secured at the distal tip end of the waveguide device or optrode. The indicator-containing substance is typically spread as a thin layer or membrane for mechanical support. Sensors of this general type are useful in measuring gas concentrations such as oxygen and carbon dioxide, monitoring the pH of a fluid, and the like. Ion concentrations can also be detected, such as potassium, sodium, calcium and metal ions.

A typical fiber optic oxygen sensor positions the sensor material at a generally distal location with the assistance of various different support means. Support means must be such as to permit interaction between the oxygen indicator and the substance being subjected to monitoring, measurement and/or detection. With certain arrangements, it is desirable to incorporate membrane components into these types of devices. Such membrane components must possess certain properties in order to be particularly advantageous. Many membrane materials have some advantageous properties but also have shortcomings. Generally speaking, the materials must be selectively permeable to oxygen molecules, and of sufficient strength to permit maneuvering of the device without concern about damage to the oxygen sensor in addition to being inert and non-solvent to the environment in which measurements are to be taken.

It is known that a luminescent aromatic molecule embedded in plastic is subject to quenching by oxygen present in the gas or liquid in contact with the plastic. This phenomenon was reported by Bergman (Nature 218:396, 1966), and a study of oxygen diffusion in plastic was reported by Shaw (Trans. Faraday Soc. 63:2181-2189, 1967). Stevens, in U.S. Pat. No. 3,612,866, ratios the luminescence intensities from luminescent materials dispersed in oxygen-permeable and oxygen-impermeable plastic films to determine oxygen concentration. Lubbers et al. in U.S. Pat. No. 4,003,707 proposed the possibility of positioning the emitting substance at the end of an optical fiber. Peterson et al. in U.S. Pat. No. 4,476,870 also employs the quenching of an emitting molecule in plastic at the end of an optical fiber. Both Lubbers and Peterson reference emission against scattered exciting light.

According to the invention disclosed in U.S. Pat. No. 6,015,715, a sensitive single-layer system is produced in such a way that the fluorescence indicators are adsorbed on to a filling material, and in connection therewith a mixture is produced with a material permeable to the analyte to be investigated. The mixture produced is then compressed under the action of pressure, advantageously at an applied pressure of 12 to $20 \times 10^4$ Pa, preferably $15 \times 10^4$ Pa on a substrate, the layer thickness being formed in dependence on the applied pressure used. The sensitive layer thus applied is polymerized, polycondensed or hardened, this preferably being carried out in an extrusion mould to be used. The layer is additionally homogenized by swelling in a fluorescence indicator solution.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator molecules. The light source, indicator molecule-containing material, high-pass filter and photodetector are configured such that at least a portion of the fluorescence emitted by the indicator molecules impacts the photodetector, generating an electrical signal which is indicative of the concentration of the analyte in the surrounding medium.

Another pO2 sensor probe utilizing an oxygen-sensitive fluorescent intermediate reagent is described in U.S. Pat. No. 4,476,870 to Peterson et al. The Peterson et al. probe includes two optical fibers ending in a jacket of porous polymer tubing. The tubing is packed with a fluorescent light-excitable dye adsorbed on a particulate polymeric support. The polymeric adsorbent is said to avoid the problem of humidity sensitivity found with inorganic adsorbents such as silica gel. The probe is calibrated by using a blue light illuminating signal and measuring both the intensity of the emitted fluorescent green signal and the intensity of the scattered blue illuminating signal. Again, none of these patents describe the high performance materials used as a medium and described in this disclosure.

Hydrocarbon and Other Environment Media In U.S. Pat. No. 6,139,798 issued to Klimant et al. on Oct. 31, 2000 entitled Sensor Membrane of an Optical Sensor, there is disclosed a sensor membrane of an optical sensor for detection of O.sub.2, H.sub.2 O.sub.2, SO.sub.2 or halogenated hydrocarbons in a sample. The membrane contains an indicator substance that is homogeneously immobilized in the polymer matrix of the sensor membrane and is, at least indirectly, in contact with the sample, changing at least one of its optical properties upon a change of the parameter to be measured. The indicator substance contains an inorganic salt of a transition metal complex with alpha-diimine ligands. The indicator substance is homogeneously distributed in the polymer matrix, which essentially consists of at least one substance belonging to the group of cellulose derivatives, polystyrenes, polytetrahydrofuranes, or their respective derivatives.

In U.S. Pat. No. 6,441,055 issued to Katerkamp et al. on Aug. 27, 2002, entitled Sensor Membrane For Determining Oxygen Concentrations And Process For The Preparation Thereof, there is disclosed sensor membranes for determining oxygen concentrations and to a process for the preparation thereof, in which, in a polymer matrix which is permeable to oxygen, an indicator is present whose optical and physicochemical properties can be influenced by the respective analytes. Starting from the disadvantages of known sensor membranes, it is the object of the Katerkamp invention to provide a sensor membrane which is thermally and also dimensionally stable, and can be prepared simply and flexibly. This object is achieved according to the invention in that the polymer matrix which contains the optical oxygen indicator is formed from a polymer containing sulfur, preferably in the main chain, particularly preferably containing sulfide and/or sulfone functionalities in the main chain.

In U.S. Pat. No. 6,254,829 issued to Hartmann et al. on Jul. 3, 2001, entitled Optochemical Sensor there is disclosed an optical sensor including a matrix containing a luminescence indicator whose luminescence may be quenched by oxygen. The optical sensor contains at least one agent capable of deactivating singlet oxygen and has an enhanced stability relative to oxygen.

The stability of a sensor against washing out of the indicator also is the topic of proposals in U.S. Pat. No. 5,070,158 to Holloway and U.S. Pat. No. 5,128,102 to Kaneko, which disclose the possibility of chemically binding indicator molecules to a polymer matrix. Another way of improving the stability of a sensor against the loss of its indicator and hence the deterioration of the photophysical properties of the membrane is set forth by Markle in U.S. Pat. No. 5,511,547. A special silicone matrix comprising polar carbinol groups serves to enhance the interaction between indicator (e.g., tris(4,7-diphenyl-1,10-phenanthroline)ruthenium(II) chloride) and matrix in order to reduce the washing out, and also the aggregation, of the indicator molecules. Those measures are, however, not suitable for substantially enhancing the photostability of the membrane per se. Finally, Jensen in U.S. Pat. No. 5,242,835 describes a method for determining the concentration of oxygen in a sample by detecting the emission of the singlet oxygen itself, which is excited by energy transmission during the extinction of the luminescence, occurring at a wavelength of approximately 1270 nm. Also, that method is prone to photodecomposition of the indicator or the matrix by exactly that reactive singlet oxygen, the latter returning into its ground state without radiation during a photochemical reaction, thus causing also the sensitizer molecules (indicators) serving the production of the singlet oxygen to be attacked.

Thus, as can be seen by the above review of the prior art there is a need for a process that produces a matrix or medium for the fabrication of optical chemical sensors and appropriate support media that can be used in the presence of non-polar volatile hydrocarbons such as those present in solvents, fuels, and other products containing volatile hydrocarbons while still having permeability to oxygen. Also there is a need for a matrix that prevents the degradation of the sensor material by preventing leaching, and accelerated photo bleaching which have been observed in sensors that do not use the new resistant materials wherein said matrix does not exhibit any signal interference.

OBJECTS AND SUMMARY OF THE INVENTION

The disclosed process produces a matrix or medium for fabrication of optical chemical sensors that can be used in the presence of non-polar volatile hydrocarbons such as those present in solvents, fuels, and other products containing volatile hydrocarbons. The matrix prevents the degradation of the sensor material by preventing leaching, and accelerated photo bleaching which have been observed in sensors that do not use the new resistant materials. In addition, the sensors do not exhibit the interference in the signal caused by hydrocarbon vapors interacting with the sensor molecules. As shown above the current standard sol-gel mediums used in optical sensors are not suitable for hydrocarbon environments. It has been shown that the sensor starts loosing sensitivity due to the penetration of fuel into the sol-gel medium and interacting with fluorophore and causes severe photo bleaching. The present invention involves the process and composition for fabricating a multi-component sol-gel designed to improve resistance to volatile hydrocarbons. The enhanced resistance to hydrocarbons allows the development of optical sensors with improved stability in hydrocarbon environment.

According to the preferred embodiment of the present invention, there is provided the following steps for fabricating the membrane: (1) Addition of a fluorinated sol gel precursor [(3,3,3-trifluoropropyl)triethoxysiloxane] to methyltrimethoxysilane (MTMS) for fabricating a multicomponent sol gel medium, (2) doping the multicomponent sol gel with tris-(4,7-diphenyl-1,10-phenanthroline)ruthenium (II) chloride, (3) coating the doped sol gel on optical fibers, and (4) thermal and/or optical curing of the coating.

The fluorinated sol gel provides resistance toward hydrocarbons due to its oleophobic properties. Methyltrimethoxysilane (MTMS) forms a glass backbone structure possessing excellent mechanical integrity and high resistance to cracking. The application of the composition may be to a fiber optic cable or other substrate via methods well know to art resulting in the deposition of a strong, fuel/non-polar hydrocarbon resistance, crack free coating.

Thus it is an object of this invention to disclose a process that produces a matrix or medium for fabrication optical chemical sensors that can be used in the presence of non-polar volatile hydrocarbons such as those present in solvents, fuels, and other products containing volatile hydrocarbons. It is a further object of this invention to disclose a matrix that prevents the degradation of the sensor material by preventing leaching, and accelerated photo bleaching which have been observed in sensors that do not use the new resistant materials.

BRIEF DESCRIPTION OF THE DRAWINGS

These and other advantages of the invention may be more clearly understood with reference to the Specification and the drawings, in which:

FIG. 1 depicts a Table showing a comparison between a standard (formulation) sensor and new formulation sensor signal intensity and lifetime change over 24 hours in air saturated with Jet Fuel.

DETAILED DESCRIPTION OF THE INVENTION

Figure 2:
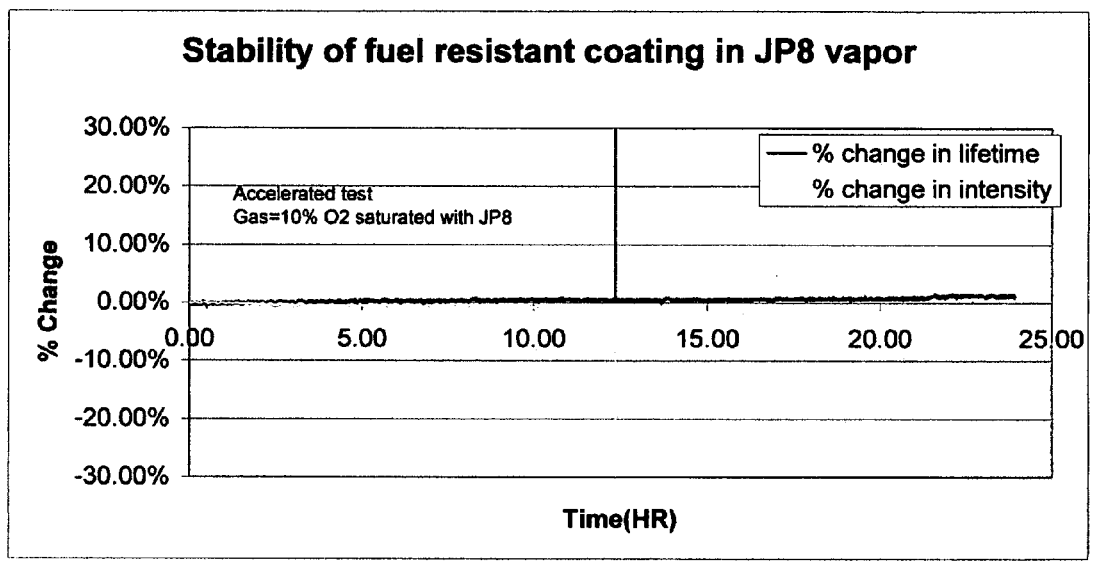
FIG. 2 depicts a graph showing the stability of Fluorescence and life time of new coating in jet fuel.

The fiber optic sensor elements of a preferred embodiment of the present invention employ the sol-gel technique to encapsulate fluorescence material sensitive to oxygen. The sol gel technique is well known in the art. An explanation of the usual process is contained in "Sol-gel Coating-based Fiber Optic O2/DO sensor," M. R. Shahriari, J. Y. Dings, J. Tongs, G. H. Sigel, *International Symposium on Optical Tools for Manufacturing and Advanced Automation, Chemical, Biomedical, and Environmental Fiber Sensors, Proc. SPIE*, V0l. 2068 (1993).

There are various routes to the manufacture of sol-gel matrices which are known to the art. Common starting materials are tetraethyl orthosilicate (TEOS) and tetramethy orthosilicate (TMOS). A common route is to mix a metal siloxane and solvent with any desired modifiers or additives and/or dopants. This sol is then encouraged to form a gel via hydrolysis with subsequent polycondensation forming certain intermediate silicate fractals, monomers, and ultimately a rigid gel structure with high porosity.

During the manufacture of the sol-gel membrane of the present invention, the indicator molecules are added. In making the preferred embodiment, a ruthenium complex (i.e., tris(4,7-diphenyl-1,10-phenanthroline)ruthenium (II) chloride molecule) is added to the solution and dispersed via mixing prior to gel formation. We have found that vigorous mixing of the sol and ruthenium together is adequate to disperse said ruthenium throughout the sol-gel material appropriately.

The preferred embodiment of the present invention provides the following steps for fabricating the membrane: (1) Addition of a fluorinated sol gel precursor [(3,3,3-trifluoropropyl)triethoxysiloxane] to methyltrimethoxysilane (MTMS) for fabricating a multicomponent sol gel medium. Other fluorinated siloxanes precursors may be used such as (tridecafluoro-1,1,2,2-tetrahydroocyyl)triethoxysilane and (tridecafluoro-1,1,2,2-tetrahydrooctyl)trimethoxysilane, but the preferred embodiment uses MTMS. Also, other organically modified metal aloxides may be used but MTMS is used in the preferred embodiment. (2) Doping the multicomponent sol gel with tris-(4,7-diphenyl-1,10-phenanthroline)ruthenium (II) chloride or other suitable photochemically stable compounds, (3) coating the doped sol gel on optical fibers or other plastic or glass surfaces, and (4) thermal and/or optical curing of the coating by mixing the coating for three (3) hours, storing the coating overnight, air aging after coating for one (1) week and thermal aging at fifty (50) degrees Centigrade overnight.

The fluorinated sol gel provides resistance toward hydrocarbons due to its oleophobic properties. Methyltrimethoxysilane (MTMS) forms a glass backbone structure possessing excellent mechanical integrity and high resistance to cracking. The application of the composition may be to a fiber optic cable or other substrate via methods well know to art resulting in the deposition of a strong, fuel/non-polar hydrocarbon resistance, crack free coating.

Experimental Results Fiber optic oxygen probes have been prepared using the new sol-gel formulation and then were exposed to air saturated with jet fuel (JP8) vapor for 24 hours. The rate at which these new probes were leached and photo bleached were measured as the decrease in fluorescent intensity and also the decrease in the fluorescence lifetime.

FIG. 1 shows a table illustrating the comparison of a standard sample sol-gel formulation encapsulated sensor and a sol gel encapsulated sensor manufactured via the preferred embodiment of the invention. The intensity decay as measured shows a 20% decay in intensity of standard formulation verses a 2% in the new formulation sensor after being subjected to the jet fuel saturated environment for 24 hours. The table also shows 4.5% decrease in $\tau$ (fluorescence lifetime) for the standard sample as compared to a less than 1% decrease in the new formulation after 24 hours in a jet fuel saturated environment.

FIG. 2 is a graphic representation showing the stability of the new fuel resistant coating of this invention over time as contained in an atmosphere of 10% free oxygen and saturated with jet fuel. The lines show the change over time in the fluorescence intensity and lifetime as being almost flat lined with drastic improvement over the formulation standard to the industry.

It is to be understood that the present invention is not limited to the methods described above, but encompasses any and all methods within the scope of the following claims.

What is claimed is:

1. A method for the manufacture of a sol gel medium coated sensor for use in environments containing volatile hydrocarbon compounds comprising the steps of:
   fabricating a multicomponent sol gel medium using a (3,3,3-trifluoropropyl)triethoxysiloxane and an aliphatic siloxane;
   doping said multicomponent sol gel medium with an appropriate sensor material such as a colorimetric or fluorescent indicator;
   mixing and storing said multicomponent sol gel medium;
   applying said doped multicomponent sol gel medium as a coating to a substrate; and,
   thermal curing of said applied doped multicomponent sol gel medium wherein said applied doped multicomponent sol gel medium is oleophobic.

2. The method of claim 1 wherein said aliphatic siloxane is methyltrimethoxysilane (MTMS).

3. The method of claim 1 wherein said sensor material is tris-(4,7-diphenyl-1,10-phenanthroline)ruthenium (II) chloride.

4. The method of claim 1 wherein said substrate is a fiber optic cable.

5. The method of claim 1 wherein the mixing and storing of said doped multicomponent sol gel medium is by mixing said doped multicomponent sol gel for three (3) hours and storing said doped multicomponent sol gel medium overnight, and wherein the thermal curing of said optical fiber coated with said doped multicomponent sol gel medium is by air aging after coating for one (1) week and then thermal aging at fifty (50) degrees Centigrade overnight.

6. A method for the manufacture of a chemical resistant oxygen sensor comprising the steps of:
   mixing together for three (3) hours (3.3.3-trifluoropropyl) triethoxysiloxane and methyltrimethoxysilane (MTMS) creating a multicomponent sol gel medium;
   doping the multicomponent sol gel medium with tris-(4,7-diphenyl-1,10-phenanthroline)ruthenium (II) chloride;
   storing said doped multicomponent sol gel medium overnight;
   coating said doped multicomponent sol gel medium on an optical fiber; and,
   curing the applied coat of doped multicomponent sol gel medium via thermal processes by air aging after coating for one (1) week and then thermal aging at fifty (50) degrees Centigrade overnight wherein said applied doped multicomponent sol gel medium is oleophobic.

* * * * *